United States Patent
Rotmensch et al.

[11] Patent Number: 6,126,909
[45] Date of Patent: Oct. 3, 2000

[54] PROCESS AND APPARATUS FOR THE PRODUCTION OF BI-212 AND A USE THEREOF

[75] Inventors: Jacob Rotmensch; Jenny L. Whitlock, both of Chicago; John J. Hines, Newark; Paul V. Harper, Glencoe, all of Ill.

[73] Assignee: Arch Development Corporation, Chicago, Ill.

[21] Appl. No.: 09/230,635

[22] PCT Filed: Aug. 26, 1997

[86] PCT No.: PCT/US97/14994

§ 371 Date: Jan. 28, 1999

§ 102(e) Date: Jan. 28, 1999

[87] PCT Pub. No.: WO98/08481

PCT Pub. Date: Mar. 5, 1998

Related U.S. Application Data

[60] Provisional application No. 60/024,567, Aug. 26, 1996.

[51] Int. Cl.[7] .............................. C01G 29/00; G21G 4/04
[52] U.S. Cl. ...................... 423/2; 423/249; 250/432 PD; 424/1.11; 210/682
[58] Field of Search ........................ 423/2, 249; 210/682; 250/432 PD; 424/1.11; 376/187

[56] References Cited

U.S. PATENT DOCUMENTS

| | | | |
|---|---|---|---|
| 2,873,170 | 2/1959 | Hyde et al. | 23/19 |
| 3,758,663 | 9/1973 | Kirby | 423/2 |
| 4,663,129 | 5/1987 | Atcher et al. | 423/2 |
| 5,030,441 | 7/1991 | Atcher et al. | 424/1.1 |
| 5,038,046 | 8/1991 | Norman et al. | 250/432 |
| 5,110,474 | 5/1992 | Horwitz et al. | 210/635 |
| 5,772,981 | 6/1998 | Govindan et al. | 424/1.49 |
| 5,817,289 | 10/1998 | Klaveness et al. | 424/1.11 |

OTHER PUBLICATIONS

Bloomer, McLaughlin, Neirinckx, Adelstein, Gordon, and Wolf, "Astatine–211 tellurim radiocolloid cures experimental ascites," *Science*, 212:340, 1981.

Dembo, "Abdominopelvic radiotherapy in ovarian cancer: a 10 year experience," *Cancer*, 55:2285, 1985.

Early, P.J. and Sodee, D.B. (eds.) *In: Radiation measurement and protection*, St. Louis, Missouri: Mosby, pp. 65–80, 1995.

Eastman Kodak Co., "Autoradiography at the light microscropic level," Kodak Tech. Bits, 1988.

(List continued on next page.)

*Primary Examiner*—Ngoclan Mai
*Attorney, Agent, or Firm*—Welsh & Katz, Ltd.

[57] ABSTRACT

A process for producing substantially radio-impurity-free Bi-212 is disclosed. An acidic feed solution containing Pb-212 is contacted with an extraction medium to bind the Pb-212 thereto. The extraction medium is rinsed with a second acid solution to remove impurities therefrom, leaving a substantially impurity-free Pb-212-laden extraction medium The Pb-212 grows on the extraction medium to form Bi-212 by radioactive decay. The Bi-212 is then eluted from the extraction medium with an acid solution to form a substantially radio-impurity-free Bi-212 acid solution. An apparatus for carving out this process and a process for the therapeutic use thereof are also disclosed.

24 Claims, 6 Drawing Sheets

OTHER PUBLICATIONS

Fisher, "The Microdosimetry of monoclonal antibodies labeled with alpha–particles," *In: Fourth International Radiophrarmaceutical Dosimetry Symposium*, A.J. Schlafke and E.E. Watson (eds.), U.S. Department of Energy, pp. 26–36, 1986.

Hall, E.J. (ed.) "Cell survival curves," *In: Radiobilogy for the radiologist* (4$^{th}$ ed.), Philadelphia, JB Lippincott Co., pp. 29–73, 1994.

Hartmann, Horak, Garmestani, Wu, Brechbiel, Kozak, Tso, Kosteiny, Gansow, Nelson, and Waldmann, "Radioimmunotherapy of nude mice bearing a human interleukin 2 receptor α–expressing lymphoma utilizing the α–emitting radionuclide–cojugated monoclonal antibody $^{212}$Bi–anti–Tac," *Canc. Res.*, 54:4362–4370, Aug., 1994.

Hartveit, The immediate cause of death in mice with ehrlich's ascites carcinoma, *Acta Path. et al., Microbiol. Scandinav.*, 65:359–365, 1965.

Harvey, "Heavy metals," *In: The Pharmacological Basis of Therapeutics*, (3$^{rd}$ ed.), L.S. Goodman and A. Gilman (eds.), New York: McMillan Co., pp. 943–975, 1965.

Horwitz, E.P.: Dietz, M.L.; Rhoads, S.; Felinto, C.; Gale, N.H.; and Houghton, J.; "A Lead–Selective Extraction Chromatogrphic Resin and its Application to the Isolation of Lead from Geological Samples," *Analytica Chimica Acta*, 292 (3):263–273, 1994.

Huneke, Pippin, Squire, Brechbiel, Gansow, and Strand, Effective α–particle–mediated radioimmunotherapy of murine leukemia, *Canc. Res.*, 52:5818–5820, Oct., 1992.

Junghan, Dobbs, Brechbiel, Mirzadeh, Raubitschek, Gansow, and Waldmann, Pharmacokinetics and bioactivity of 1, 4, 7, 10–tetra–azacylododecane N, N', N", N'"–tetraacetic acid (DOTA)–bismuth–conjugated anti–conjugated antitact antibody for α–emitter ($^{212}$Bi) therapy, *Canc. Res.*, 53:5683–5689, Dec., 1993.

Kozak, Atcher, Gansow, Friedman, Hines, and Waldmann, "Bismuth–212–labeled anti–tac monoclonal antibody: α–particle–emitting radionuclides as modalities for radioimmunotherapy," *Proc. natl. Acad. Sci. U.S.A.*, 83:474–478, Jan., 1986.

Loevinger, R., Budinger, T.F., and Watson, E.E. (eds.) "Primer part 1, MIRD primer for absorbed dose calculations," *Soc. of Nucl. med.*, new York, Jan. 22, 1988.

rotmensch, Atcher, Hines, Grdina, Schwartz, Toohill and Herbst, "Development of d–emitting radionuclide lead–212 for the potential treatment of ovarious carcinoma," *Am. J. Obstet. Gynecol.*, 60:789–797, 1989.

Rotmensch, Atcher, Hines, Toohill, and Herbst, "Comparison of short–lived high–LET α–emitting radionuclides lead–21 '2 and bismuth–212 to low–LET x–rays on ovarian carcinoma," *Gynecol Onvol.*, 35:297–300, 1989.

Schwartz, Shadley, Atcher, Tang, Whitlock, and Rotmensch, "Comparison of radon–daughter–induced effects of repair proficient and repair deficient CHO cell lines," *Environ. Mol. Mutagen.* 16:178–184, 1990.

Selman, "Medical use of radionuclides," *In: The Basic Physics of Radiation Therapy*, (2$^{nd}$ ed.), Charles C. Thomas, Publisher, Springfield, Illinois pp. 472–533, 1976.

Shadley, Whitlock, Rotmensch, Atcher, Tang, and Schwartz, "The effects of radon daughter α–particle irradiation in K1 and xrs–5 CHO cell lines," *Mutation Res.*, 248:73–83, 1991.

Simonson, Ultee, Hauler, and Alvarex, "Radioimmunotherapy of peritoneal human colon cancer xenografts with site–specifically modified $^{212}$Bi–labeled antibody," *Canc. Res.*, 50:985s–988s, Feb. 1990.

Thigpen, Blessing, and Vance, "Chemotherapy in ovarian cancer: present role and future prospects," *Semin, Oncol.*, 16 (Suppl. 6):58, 1989.

Weiser, Burke, Heller, Woodward, Hoskins, and Park, "Determinant of survival of patients with epithelial ovarian cancer following whole abdomen irradiation (WAR)," *Gynecol. Oncol.*, 30:201, 1988.

Young, Walton, Ellenberg, Homesley, Wilbanks, Decker, Miller, Park and Majors, "Adjuvant therapy in Stage I and Stage II epithelial ovarian cancer," *N. Engl. J. Med.*, 322:1021, 1990.

Zucchini and Friedman, "Isotopic generator for $^{212}$Pb and $^{212}$Bi," *Int. J. Nucl. med. Biol.*, 9:83–84, 1982.

PROCESS AND APPARATUS FOR THE PRODUCTION OF BI-212 AND A USE THEREOF

This application claims the benefit of U.S. Provisional application Ser. No. 60/024,567, filed Aug. 26, 1996.

DESCRIPTION

1. Technical Field

This invention relates to a process and apparatus for the production of bismuth-212 (Bi-212) and a use for Bi-212. More particularly, the invention relates to a process and apparatus for the production of substantially radio-impurity-free bismuth-212 from a starting material containing lead-212 and a therapeutic use for the bismuth-212.

2. Background of the Invention

Ovarian carcinoma has the highest mortality rate of any gynecologic cancer. This is due, in part, to the spread of the disease outside of the pelvis by the time the disease is diagnosed. Cytoreductive surgery and therapy have improved the overall survival rate of patients with ovarian carcinoma. However, relapses have been observed even after apparent complete remission.

Initial treatment of patients whose cancers have reached stages III and IV with multiple chemotherapy agents yields positive responses in about 90 percent of the patients. However, after four years, only about 30 percent of the patients are expected to survive. Thigpen et al., *Semin. Oncol.*, 16(*Suppl.* 6):58 (1989). Current treatment strategies following relapse include intraperitoneal chemotherapy and abdominopelvic external beam therapy. These treatments have usually been found to be ineffective.

Radiation therapy, such as X-ray therapy, has been observed to be the most effective treatment for microscopic disease. Microscopic disease refers to the layers of cells remaining after removal of a tumor, cells of a tumor that are beginning to form and the first few cell layers of tumor growth and formation. The use of radiation therapy is limited to the radio tolerance of normal cells and by technical problems encountered in delivering tumoricidal doses.

In addition, it is believed that when the tumor does not respond to conventional radiation therapy this may be due, in part, to the quality of radiation that is used. For example, X-ray therapy is low-LET (linear energy transfer), is sparsely ionizing and its effectiveness is dependent on cellular oxygen.

Radionuclide therapy using chromic phosphate (P-32), which is a low-LET beta-emitter, has exhibited some level of success. A five-year survival rate of 81 percent for the treatment of microscopic disease has been reported for patients with stage I and stage II disease. Young et al., *N. Eng. J. Med.*, 322:1021 (1990). Nevertheless, similar to X-ray therapy, P-32 is low-LET, is sparsely ionizing and its effectiveness is dependent on cellular oxygen.

Alpha-emitting radionuclides have also been found to be effective in the treatment and eradication of microscopic carcinoma in animal models. This is believed to be a result of the densely ionizing radiation that is emitted during alpha-decay, and the cellular oxygen independence of the affect of an alpha particle on the disease.

It has been shown that lead-212 (Pb-212) and astatine-211 (At-211) are effective in the treatment and eradication of microscopic carcinoma. The effectiveness of Pb-212 in treating the carcinoma is due to its subsequent decay to Bi-212, which is an alpha-emitting radionuclide. Pb-212, itself, is not as effective as the alpha-emitting Bi-212 radionuclide.

Known processes for producing alpha particle-emitting nuclides such as At-211 are limited in that they generally require the use of particle accelerators for production of the nuclides. Moreover, the radionuclides so produced are often contaminated with radio-impurities that are difficult to filter out or otherwise remove from a desired nuclide. It has also been found that such nuclides that are administered intraperitoneally using a complexing agent such as Pb-212/ferrous hydroxide do not have the desired property of even distribution.

Bismuth-212, which as noted above, is an alpha-emitting radionuclide, has recently been found to exhibit the desirable properties associated with At-211 in providing highly ionizing radiation and exhibiting cellular oxygen independence. Moreover, certain formulations of Bi-212 made in accordance with this invention as discussed hereinafter have also been found to overcome the distributional problems encountered with complexed Pb-212 and At-211 upon intraperitoneal administration. In addition, Bi-212 has a half-life of 60.6 minutes, which makes this isotope useful for intraperitoneal treatment because it emits its radiation while its distribution in the peritoneal fluid is uniform.

Nevertheless, problems have been encountered in the production of Bi-212. The production of Bi-212 is dependent upon natural radioactive decay, and impurities are typically present in the Bi-212 final product. Bi-212 is produced from a Thorium-228 (Th-228) source. The decay of Th-228 produces radium-224 (Ra-224) which decays to Radon-220 (Rn-220), which decays to Polonium-216 (Po-216), which decays to Pb-212, which in turn decays to Bi-212. Those skilled in the art will recognize that impurities (e.g.; the parent isotopes and daughter isotopes of Bi--212) can adversely affect treatment of and eradication of the carcinoma.

Moreover, because of the highly ionizing nature of the parent isotopes that decay to Bi-212 and in particular, the alpha-emitting isotopes, and because of the relatively short half-life of Bi-212, it would be more desirable to produce Bi-212 at a location remote from a Th-228 source, and as physically close to the patient as possible. It would, of course, be most beneficial to produce the isotope at the patient's "bed-side" to reduce the stress on the patient and reduce or eliminate the need for specifically designed facilities for radiotherapy.

Accordingly, there continues to be a need for a process and apparatus for the production of Bi-212 that is substantially free of radio-impurities. There is also a need for a process and apparatus that permit local production of Bi-212 at a location remote from the associated primary Th-228 source. Such an apparatus should further be sufficiently portable so it can be transported to a patient for administration of and treatment with Bi-212 without the need for special facilities such as intensive radiation shielding. The disclosure that follows provides one such apparatus and a method or process for its use, as well as a therapeutic process for using the Bi-212 so prepared.

SUMMARY OF THE INVENTION

A process of producing substantially radio-impurity-free Bi-212 is contemplated. That process comprises the steps of contacting an acidic Pb-212 feed solution containing Pb-212 or a Pb-212-generating material with an extraction medium having a plurality of high affinity Pb-212 binding sites thereon, to form a Pb-212-laden extraction medium that can contain contaminants. The Pb-212-laden extraction medium is rinsed with a second acid solution to remove contaminants therefrom and form a substantially impurity-free Pb-212-laden extraction medium. The Pb-212 on the extraction medium is incubated (maintained) for a predetermined period of time so as to form Bi-212 from the Pb-212 by radioactive decay. A third acid solution is introduced to the Pb-212-laden extraction medium to release the Bi-212 therefrom, and form an acid solution containing Bi-212. The solution is eluted from the impurity-free Pb-212-laden extraction medium to form a substantially radio-impurity-free Bi-212 acid solution. That acid solution can be subsequently neutralized for administration to a patient.

In a preferred process, a first acid solution is introduced to a starting material having Pb-212 or a Pb-212-generating material to form the acidic Pb-212 feed solution.

In another preferred embodiment, the substantially radio-impurity-free Bi-212 acid solution that is eluted from the extraction medium is contacted with a subsequent extraction medium also having high Pb-212 affinity characteristics to remove Pb-212 that can break through from the first extraction medium contact. In a most preferred process, the first and second acid solutions are hydrochloric acid in concentrations of about 0.9 N to about 2.0 N.

The substantially radio-impurity-free Bi-212 acid solution can be neutralized with, for example, sodium hydroxide (NaOH) or any other pharmaceutically acceptable base and diluted to form an isotonic solution for patient administration.

An apparatus for producing substantially radio-impurity-free Bi-212 from a starting material of Pb-212 or a Pb-212 generating material includes an extraction medium having an affinity for binding Pb-212 thereto and a lower affinity for binding Pi-212 thereto. A first acid supply is in flow communication with the starting material and is adapted to supply a first acid solution to carry the Pb-212 to the extraction medium. The apparatus includes a first vessel adapted to retain the extraction medium and to maintain contact between the extraction medium and the first acid. A second acid solution supply is in flow communication with the vessel and is adapted to supply a second acid thereto.

The apparatus includes a mixing chamber in flow communication with the vessel adapted to receive a liquid solution from the vessel. The mixing chamber includes a plurality of inputs for adding solutions to the mixing chamber to, for example, neutralize and dilute the solution therein. A discharge line is in flow communication with the mixing chamber for discharging liquid therefrom.

A preferred embodiment of the apparatus includes a second vessel positioned between the first vessel and the mixing chamber. The second vessel is loaded with an extraction medium that also has high Pb-212 affinity characteristics and low Bi-212 affinity characteristics.

The present process and apparatus facilitate the production of substantially radio-impurity-free Bi-212, and the preparation of a Bi-212 solution for patient administration. The apparatus can be configured for transport to a patient and for local production of Bi-212 for rapid administration. The present process and apparatus remove the constraints of known processes and apparatuses, particularly relating to the production of the radio-nuclide and the purification thereof.

A process for treating target cells includes contacting target cells with a biologically effective amount of a pharmaceutically acceptable composition that comprises an aqueous suspension of substantially radio-impurity-free Bi-212. In a preferred process, the Bi-212 is uncomplexed. The target cells can be of microscopic carcinoma and the Bi-212 suspension can be administered to a host mammal in need thereof intrapertioneally.

Advantageously, the present process for producing Bi-212 produces a substantially radio-impurity-free Bi-212 acid solution that is free of contamination from Bi-212 parent radionuclides. Thus, although Bi-212 decay products exist in the solution because of the decay of Bi-212, the level of other radioactive nuclide present is not measurable.

An apparatus for producing the substantially radio-impurity-free Bi-212 acid solution is sufficiently compact that the apparatus can be readily transported to and from a patient's bed-side without special facilities, such as extensive shielding. The apparatus is contained in a relatively compact lead-shielded container that permits ready transportation. Moreover, the apparatus permits the production of Bi-212 remote from the before-noted Th-228 source.

The substantially radio-impurity-free Bi-212 that is produced can be used in a variety of therapeutic applications. Adventageously, the Bi-212 that has been prepared for therapeutic use distributes evenly within the peritoneal fluid during the time that the Bi-212 "delivers" its radiation to target cells. That is, unlike known alpha-emitting preparations such as Pb-212/ferrous hydroxide, which "clump" within the peritoneal cavity, a contemplated Bi-212 preparation distributes evenly to contact target cells within the host mammal.

Other features and advantages of the present invention will be apparent from the following detailed description, the accompanying drawings, and the appended claims.

BRIEF DESCRIPTION OF THE FIGURES

In the figures forming a portion of this disclosure.

DETAILED DESCRIPTION OF THE PREFERRED EMBODIMENTS

Figure 1:
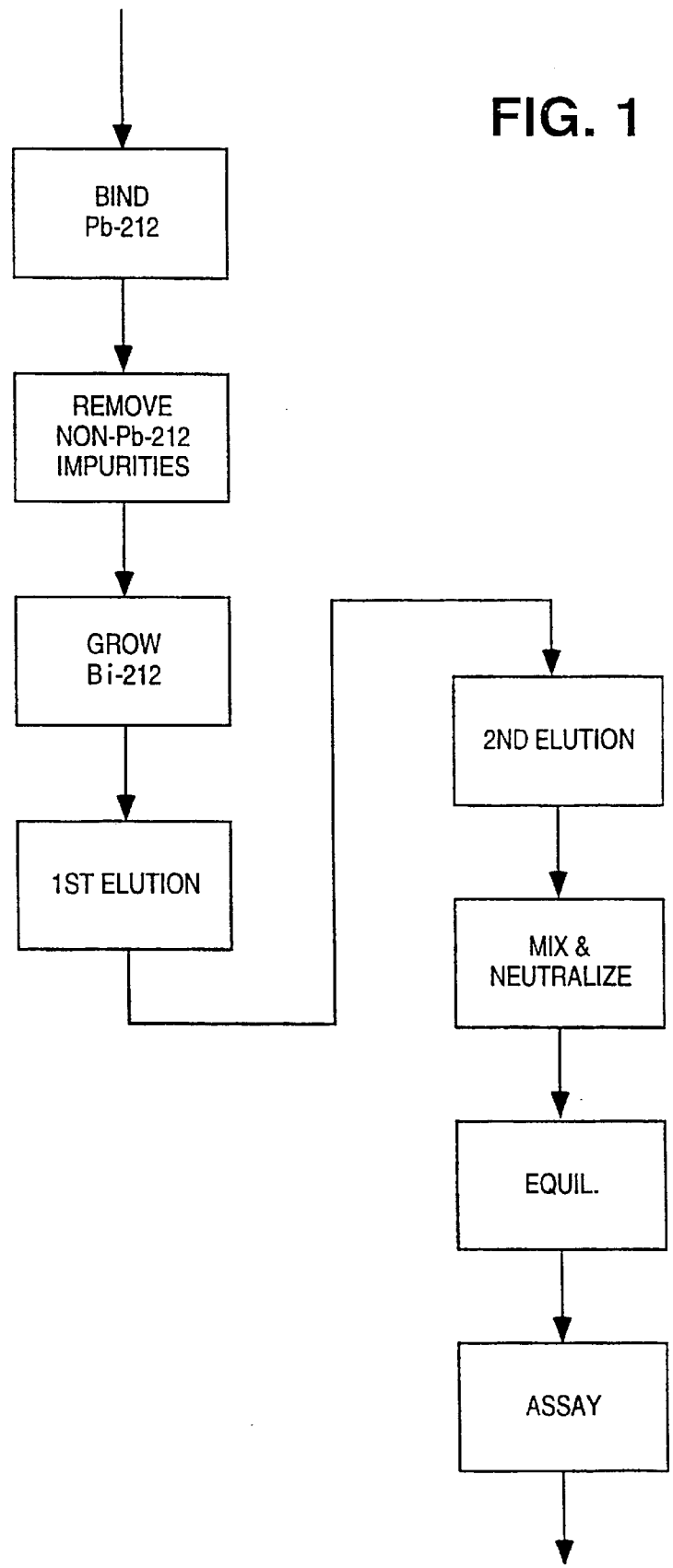
FIG. 1 is a simplified flow diagram of a process for the production of relatively radio-impurity-free Bi-212, embodying the principles of the present invention.

Although the present invention is susceptible of embodiment in various forms, there is shown in the drawings and will hereinafter be described a presently preferred process and a presently preferred embodiment of an apparatus with the understanding that the present disclosure is to be considered an exemplification of the invention and is not intended to limit the invention to the specific process and apparatus illustrated.

Referring now to the figures and particularly to FIG. 1, there is shown a simplified flow diagram depicting a process for producing substantially radio-impurity-free Bi-212. Bi-212 is produced from a starting material containing lead-212 (Pb-212) or a Pb-212-generating material such as radium-224 (Ra-224). The starting material can be provided, for example, in accordance with the teachings of U.S. Pat. No. 4,663,129 to Atcher et al., whose disclosures are incorporated herein by reference.

In the present process, a first acid solution is introduced to the starting material to a form a Pb-212 feed solution. The Pb-212 feed solution is contacted with an extraction medium having a plurality of binding sites thereon adapted to bind the Pb-212 thereto, and form a Pb-212-laden extraction medium and less strongly bound contaminants. The Pb-212-laden extraction medium is rinsed with a second acid solution to remove the contaminants therefrom and to form a substantially radio-impurity-free Pb-212-laden extraction medium.

Figure 3:
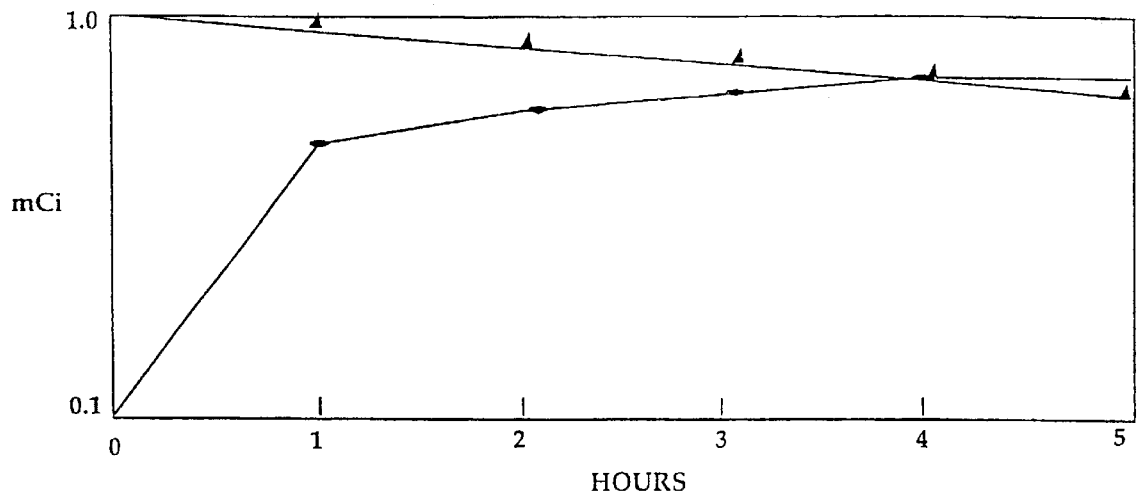
FIG. 3 is a graphic illustration of the decay rate of Pb-212 (triangles) in milliCuries (mCi) relative to the production rate of Bi-212 (circles)
Figure 4:
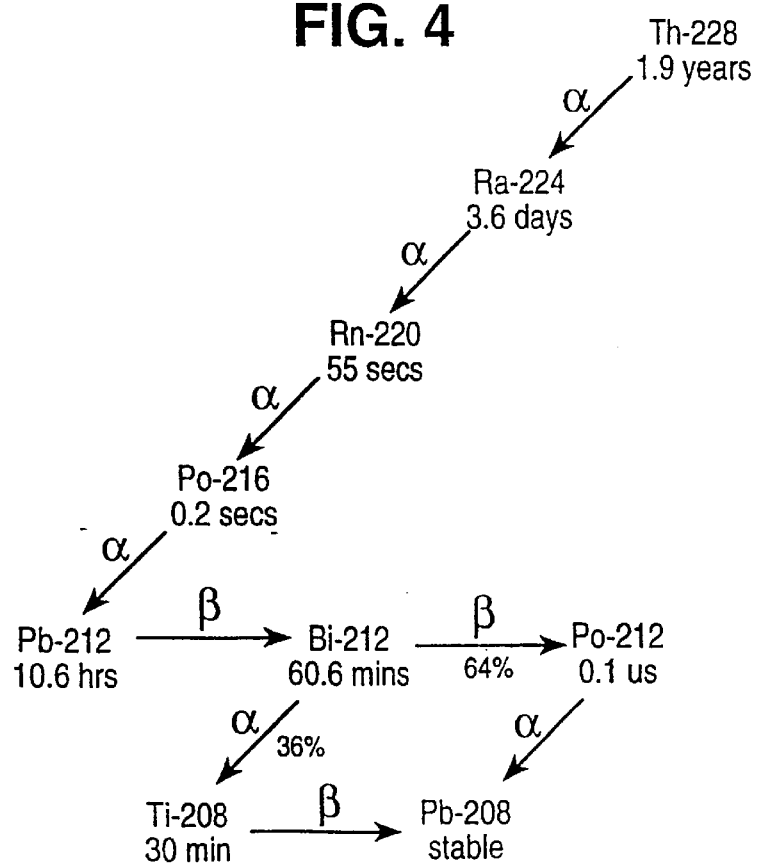
FIG. 4 is an illustration of the Th-228 decay chain showing the decay products thereof including radium-224, lead-212 and bismuth-212, the decay process (alpha or beta) and half-lives of the decay products.

The impurity-free Pb-212-laden extraction medium is incubated (is maintained) for a predetermined period of time so as to form Bi-212 from Pb-212 by radioactive decay as illustrated in FIG. 3. This type of maintenance step is often referred to in the art as "growing" a desired radionuclide. A third acid solution is introduced to the extraction medium to release the Bi-212 therefrom, to form a Bi-212 acid solution. The Bi-212 acid solution is then eluted from the Pb-212-laden extraction medium. The eluant is a substantially radio-impurity-free Bi-212 acid solution; i.e., the solution contains Bi-212 and its decay products, but is free of decay products from radionuclides other than Bi-212. That is, the resulting solution is greater than 95 percent radio-impurity-free, and more preferably greater than 99 percent radio-impurity-free.

Bi-212 is produced from Pb-212 by radioactive decay. As shown in FIG. 3, Bi-212 is a daughter product of Pb-212. Pb-212 has a half-life of about 10.6 hours, and decays to Bi-212 through beta decay. The Pb-212 is purified to remove any radio-impurities that may be present, and is permitted to decay to produce Bi-212. The Bi-212 is then purified to form a relatively radio-impurity free stream of Bi-212.

An acid solution is used to transfer the Pb-212 from a source, such as a radium generator as described in the aforementioned Atcher patent, to the extraction medium. In a present embodiment, the extraction medium is a solid phase-supported (e.g., resin-supported) extractant, referred to as an extraction chromatographic resin. The extraction medium has a plurality of binding sites that have a relatively high affinity for ions of Pb-212 and a lower affinity for ions of Bi-212, as well as ions of isotopes of thorium and radium, such as Th-228 and Ra-224.

In the current embodiment, the column is loaded with "Sr Resin™", an analytical resin available from Eichrom Industries, Inc. of Darien, Ill., that is described in U.S. Pat. No. 5,110,474, which disclosure is incorporated by reference. Briefly, the Sr Resin comprises an inert resin substrate upon which is dispersed a solution of the extractant, namely, a crown either dissolved in a liquid diluent.

The diluent is an organic compound that has (i) a high boiling point; i.e. about 1700 to 200° C., (ii) limited or no solubility in water, (iii) is capable of dissolving from about 0.5 to 6.0 M water, and is a material (iv) in which the crown ether is soluble. These diluents include alcohols, ketones, carboxylic acids and esters. Suitable alcohols include 1-octanol, which is most preferred, although 1-heptanol and 1-decanol are also satisfactory. The carboxylic acids include octanoic acid, which is preferred, in addition to heptanoic and hexanoic acids. Exemplary ketones include 2-hexanone and 4-methyl-2-pentanones, whereas esters include butyl acetate and amyl acetate.

The macrocyclic polyether can be any of the dicyclohexano crown ethers such as dicyclohexano-18-Crown-6, dicyclohexano 21-Crown-7, or dicyclohexano-24-Crown-8. The preferred crown ethers have the formula: 4,4' (5') [R,R') dicyclohexano]-18-Crown-6, where R and R' are one or more members selected from the group consisting of H and straight chain or branched alkyls containing 1 to 12 carbons. Examples include, methyl, propyl, isobutyl, t-butyl, hexyl, and heptyl. The preferred ethers include dicyclohexano-18-crown-6 (DCH18C6) and bis-methylcyclohexano-18-crown-6 (DMeCH18C6). The most preferred ether is bis-4,4' (5') [(t-butyl)cyclohexano]-18-Crown-6 (Dt-BuCH18C6).

The amount of crown ether in the diluent can vary depending upon the particular form of the ether. For example, a concentration of about 0.1 to about 0.5 M of the most preferred t-butyl form (Dt-BuCH18C6) of the above-noted preferred crown ether in the diluent is satisfactory, with about 0.2 M being the most preferred. When the hydrogen form is used, the concentration can vary from about 0.25 to about 0.5 M. Concentrations above about 0.5 M of the crown ether in the diluent do not improve lead recovery when R and R' are H.

The preferred Sr Resin™ utilizes an inert resin substrate that is a non-ionic acrylic ester polymer bead resin such as Amberlite®XAD-7 (60 percent to 70 percent by weight) having a coating layer thereon of a crown ether such as 4,4'(5')di-t-butylcyclohexane-18-crown-6 (bis-t-butyl-cis-dicyclohexane-18-crown-6) (20 percent to 25 weight percent) dissolved in n-octanol (5 percent to 20 weight percent), having an extractant loading of 40 weight percent. E. P. Horwitz et al., *Solvent Extractions and Ion Exchange*, 10(2),313–16 (1992).

It has also been observed that Pb Resin™, a related resin, also available from Eichrom Industries, is also useful for purifying and accumulating Pb-212 for the production of Bi-212. Pb Resin™ has similar properties to Sr Resin™ except that a higher molecular weight alcohol; i.e., isodecanol, is used in the manufacture of Pb Resins. E. P. Horwitz et al., *Analytica Chimica Acta*, 292, 263–73 (1994). It has been observed that Pb Resin™ permits subsequent extraction of the Pb-212 from the resin, whereas it has been observed that Pb-212 becomes essentially irreversibly bound to the Sr Resin™.

It is to be noted that the present process can be carried out by contacting the Pb-212 feed solution with a medium other than the above-noted solid phase-supported extractant. For example, it is contemplated that the Pb-212 feed solution can be contacted with the extractant (e.g., the crown ether dissolved in the liquid diluent) in a liquid-liquid extraction process. The extractant and exemplary processes for the use thereof are disclosed in U.S. Pat. No. 5,100,585 to Horwitz et al., which disclosure is incorporated by reference. Such other processes are within the scope of the present invention.

The Pb-212 is transferred to the resin-loaded column in an acidic elutriant solution. A preferred elutriant is hydrochloric acid (HCl) having a concentration of about 0.5 N to about 4.0 N. It has been observed that when Ra-224 is used as the starting material, the use of acid concentrations above about 3.0 N can cause breakthrough of the Ra-224 from the resin column. As such, the concentration of the acidic elutriant can be adjusted accordingly to prevent radium breakthrough through the resin column. Nitric acid has also been shown to be an effective elutriant. Other monobasic acids, such as hydroiodic acid, can also function effectively as elutriants.

The loaded column is then rinsed with an acid solution, such as HCl, to remove radio-impurities therefrom. Preferably, the acid rinse solution has a concentration of about 0.5 N to about 4.0 N, and most preferably about 2.0 N. The impurities present on the Pb-212-loaded resin column can include Bi-212, Th-228 and Ra-224. Because the Sr Resin™ has a higher affinity for Pb-212 than other radioisotopes, the impurities are rinsed from the resin by the acid solution. The acid solution containing the impurities is forwarded from the column to a waste receptacle. The wastes are handled and treated in accordance with good practices as will be recognized by those skilled in the art.

After the column is rinsed, the column contains a substantially impurity-free Pb-212-loaded resin complex. The Pb-212 bound to the resin is then allowed to incubate on the column to "grow" Bi-212. As will be recognized by those skilled in the art, Pb-212 has a half-life of about 10.6 hours. The decay of Pb-212 produces, by beta decay, the daughter Bi-212, which has a half-life of about 60.6 minutes.

As the Pb-212 decays, the concentration of Bi-212 on the resin increases. A graphic representation of the relative decay and production rates of Pb-212 and Bi-212 is illustrated in FIG. 3. As is apparent from FIG. 3, the concentration of Bi-212 increases significantly at first and reaches a maximum yield at about four hours. However, after about two hours, the yield of Bi-212 is sufficiently close to the maximum yield to elute the Bi-212 from the column in a batch processing mode. It will be recognized by those skilled in the art that the present process is not limited to a batch processing method. Rather, steady state production and elution of Bi-212 is contemplated by the present process, and is within the scope of the present invention.

After the Bi-212 has been permitted to grow for a predetermined period of time, the Bi-212 is eluted from the column using an acid solution. A preferred acid for eluting the Bi-212 is HCl in a concentration of about 0.5 N to about 1.5 N, and most preferably about 0.9 N. Other acids can be used to elute the Bi-212, such as nitric acid, hydroiodic acid and the like. As the acid contacts the resin, the Bi-212 is carried away by the solution, whereas the Pb-212 remains bound to the resin. The resulting solution contains substantially radio-impurity-free Bi-212. In usual and most preferred practice, the solution is 99.99 percent free of radio-impurities.

In a preferred process, the substantially radio-impurity-free Bi-212 acid solution is fed into a subsequent column containing a quantity of Sr Resin™. Because of the resin's high affinity for Pb-212, any Pb-212 that may have broken through from the first column is bound to and captured by the second column during contact of the Bi-212 acid solution with the resin. The Bi-212 is eluted from the resin in the second column using an acid solution similar to that used to elute the Bi-212 from the first column. The Bi-212 passes through the second resin column unaffected and ready for preparation for patient administration.

To prepare the substantially radio-impurity-free Bi-212 acid solution for patient administration, the solution is transferred to a neutralizing and dilution chamber. The solution is neutralized with an appropriate amount of a base, such as sodium hydroxide (NaOH) or another pharmaceutically acceptable base, and is diluted to produce an isotonic Bi-212-containing preparation. NaOH is a preferred neutralization agent because it produces a saline solution when HCl is used as the elutriant. An indicator solution, such as phenolsulfonthaline can be added to the preparation to monitor the pH value thereof. The preparation can be diluted with deionized water to produce an isotonic preparation, e.g., about 0.85 percent saline, for patient administration.

The Bi-212-containing preparation is assayed, prior to administration to the patient, to determine the activity of the final product. As will be recognized by those skilled in the art, the decay of Bi-212 produces the short lived daughter product thallium-208 (Tl-208). Tl-208 is a high energy beta-gamma emitter having a half-life of about 3.0 minutes. As such, the Bi-212 is held for about 15 minutes prior to assaying, to permit the Tl-208 to reach equilibrium with the Bi-212. After assaying the preparation, it can be administered to a patient in accordance with principles that will be recognized by those skilled in the art.

Figure 2:
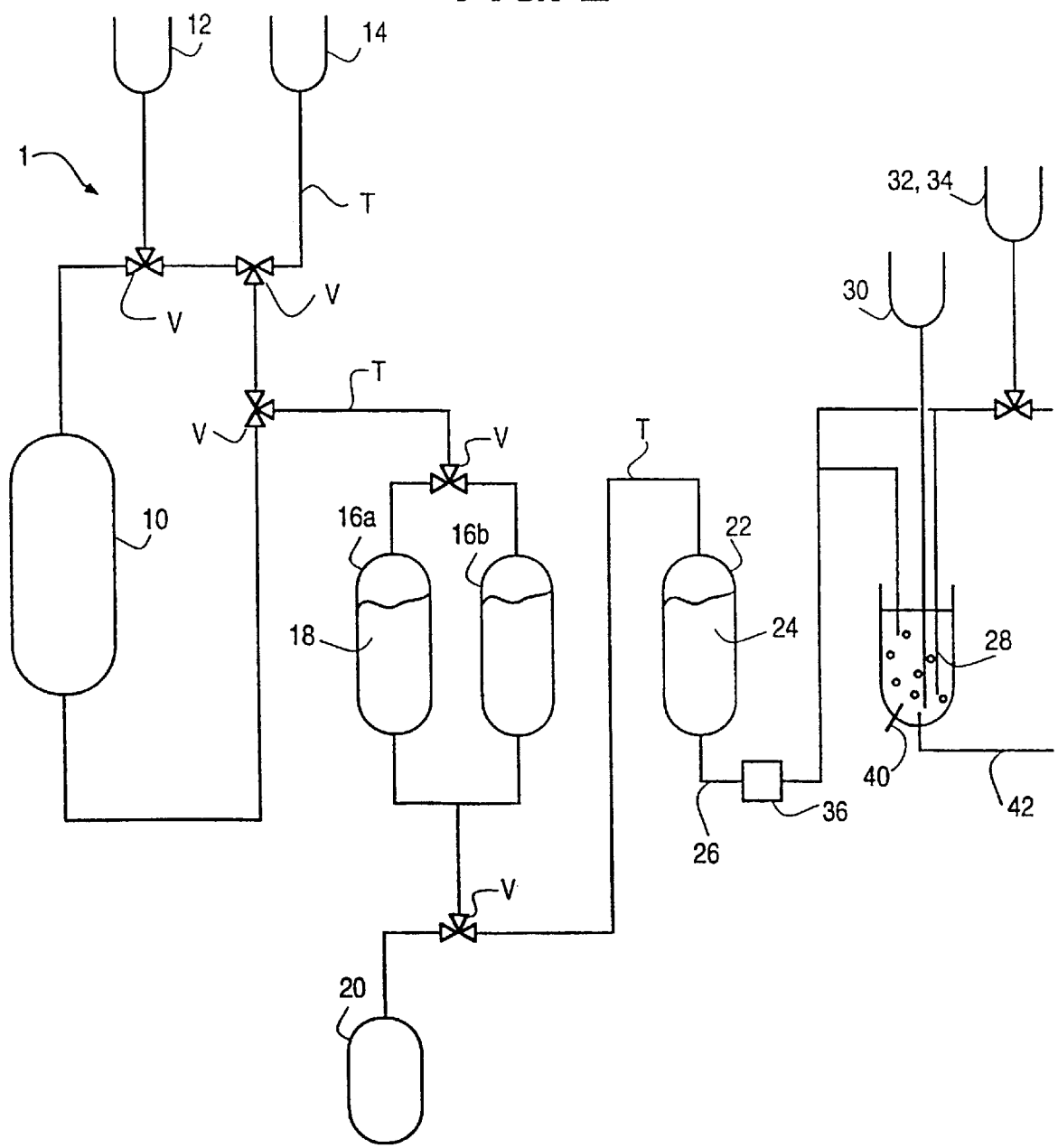
FIG. 2 is a schematic arrangement of an apparatus for the production of Bi-212.

A schematic arrangement of an apparatus 1 that is used to carry out the present process is illustrated in FIG. 2. The apparatus includes a source or starting material having Pb-212 or a Pb-212 generating material. In a current embodiment, the starting material is provided by the radium generator 10 as described in the aforementioned patent to Atcher et al.

In the illustrated embodiment, the generator 10 is in flow communication with a pair of acid solution storage sources 12, 14 for providing aqueous acid solutions to the generator. Flow communication is provided by tubing t, such as Tygon® tubing extending between the acid sources 12, 14 and the generator 10. The storage sources 12, 14 contain different concentrations of, for example, HCl, at concentrations of 2.0 N and 0.9 N, respectively. HCl at different concentrations, as well as other acids can be stored in the storage sources 12, 14. Valves v are positioned in the system 1 to initiate and terminate the flow of acid to the generator 10.

The generator 10 is also in flow communication with a first column 16, and preferably, a pair of identical "first" columns 16a. For purposes of the present discussion, reference will be made to a first column. It is to be understood that reference to the first column is to one of the pair of first columns.

In a preferred embodiment, the first column 16 contains a predetermined quantity of an extraction medium 18, such as the aforementioned Sr Resin. As is readily apparent from FIG. 2, the apparatus 1 is configured such that one of the two columns 16a can be in service while the other column 16b is idle. This arrangement provides redundancy in the system 1, and further permits extended use time of the system 1 by extending the process capacity thereof.

It is in the first column 16a, b that the Pb-212 is contacted with the extraction medium or resin 18. The Pb-212 binds with the resin 18 to form the Pb-212 laden resin. The Pb-212 laden resin is then rinsed with, for example, 2.0 N HCl to remove impurities, and is bound to the resin, to grow the Bi-212.

After a predetermined growth period, the Bi-212 is eluted from the column using, for example, 0.9 N HCl from the acid source 14. As can be seen from FIG. 2, the tubing t from the acid sources 12, 14 is configured using three-way valves to provide acid to either the generator 10 or to the first column 16.

The discharge from the "first" column can be direct to either a waste receptacle 20 or to a "second" column 22. Referring to the previously described process, the discharge from the first column 16 is a substantially impurity-free Bi-212 acid solution.

The discharge that is directed to the second column 22, the eluant of the first column 16, is contacted with a similar extraction medium 24 as that that is loaded into the first column 16. The medium 24 in the second column 22 thus serves to remove any Pb-212 that may have broken through from the first column 16.

The discharge from the second column 22 can be directed to a clean-up column 36. The clean-up column 36 can include a quantity of material to absorb any extractant or solvent that may have been removed from the Sr Resin™ and carried out of the column 22. It is contemplated that a non-ionic acrylic ester polymer bead resin, such as that used to support the extractant in the Sr Resin™ can be used in the clean-up column 36. Alternately, the clean-up column 36 can be combined into the column 22, and can be disposed at about the bottom of the column 22 to absorb any extractant or solvent that may be carried from the Sr Resin™.

The discharge 26 from the second column 22 is directed to a mixing and neutralization chamber 28. The chamber 28 includes various feed lines, such as a NaOH feed line 30 for providing a neutralizing agent to neutralize the acid solution, a deionized (preferably sterile and pyrogen-free) water feed line 32 for diluting the Bi-212 solution and for rinsing the chamber 28 and an isotonic solution feed line 34 for diluting the solution prior to patient administration.

In one embodiment, mixing is provided to the chamber 28 by gas injection to a bubbler system 40. Alternately, a magnetic stirrer (not shown) or like stirring device can be used to mix the solution. Essentially, the solution in the chamber 28 is mixed by agitation provided by gas, such as air, forced into the liquid or by, for example, mechanical agitation. The final product, ready for patient administration is discharged through a discharge line 42.

The waste receptacle 20 is adapted to receive liquid and gaseous wastes generated during the Bi-212 production process. Due to the possibility of generating radon-220 (Rn-220), the system 1 is configured to receive and filter gases that can be produced during the process. The design and configuration of such a gaseous waste storage and processing system is not within the scope of the present invention, and will be recognized by those skilled in the art.

As can be seen from FIG. 2, the system 1 includes a plurality of valves v positioned between the various liquid sources, columns and chambers to direct flow to the desired equipment to affect the desired process steps. In a preferred embodiment, the valves are remotely actuated, such as by solenoid actuators. This can considerably reduce radiation exposure to personnel.

The apparatus 1 can be subjected to high levels of radioactivity, and is a source of potentially high levels of radiation exposure when in use. Because of the nature of the radioactive sources used, e.g., the radium generator 10, and the radioisotopes produced thereby, the apparatus 1 is preferably housed in a radiologically shielded chamber or housing (not shown). Metallic lead is recognized as a preferred material for radiological shielding because of its high radiation attenuation properties. Moreover, because the physical apparatus 1 can be transported to a patient, rather than transporting the patient to the apparatus 1, lead is a preferred shielding material to reduce the overall physical size of the apparatus. In a present embodiment, the housing has about 5 to 6 inches of lead shielding.

In a present embodiment, the apparatus 1 is carried by a sleeve (not shown) within the shielded housing. In order to maintain the integrity of the process generally, and in particular the final product, a titanium or like, highly corrosion resistant sleeve is positioned in the housing and is configured to carry all of the process equipment, including the generator 10, the columns 16, 22, the mixing and neutralization chamber 28 and the waste receptacle 20.

As will be recognizable to be able to monitor the process both visually and radiologically, a periscope-like viewing port, a fiber optic viewing apparatus or like device can be positioned in the housing, or the housing can be configured to permit insertion and withdrawal of such a visual monitoring device. In addition, it has been found that the it is desirable to be able to radiologically monitor the mixing and neutralizing chamber 28 and the waste receptacle 20. As such, openings can be provided within the housing, while maintaining radiological control of the system, such that a remote radiation detector or like monitoring device can be used to determine the radiation emitted from the mixing chamber 28 and the waste receptacle 20.

When operating in batch mode, to produce a maximum yield of Bi-212, it has been found that it is most effective to elute the Bi-212 from the first column after an incubation or growth period of about two hours, and to elute the Bi-212 in successive intervals of about two hours. It has been found that a Bi-212 yield of about 79 percent of the theoretical yield can be achieved using 0.9 N HCl as the eluting solution. The theoretical yield of Bi-212 from the decay of Pb-212 is determined by the expression:

$$\text{Bi-212} = [\text{Pb}]_{20} \, (\lambda_{Bi}/\lambda_{Bi}-\lambda_{Pb}) \, [\exp(-\lambda_{Pb}t)] - [-\exp(-\lambda_{Bi}t)]$$

where $\lambda_{Bi} = 0.6863$, $\lambda_{Pb} = 0.0654$, $\lambda = \ln 2/t_{1/2}$, and t is the elution interval.

Table 1 illustrates the theoretical yield of Bi-212 at varying elution intervals, and at varying periods of "growth" of Bi-212.

TABLE 1

CALCULATED YIELD OF Bi-212 IN mCi
OBTAINED FROM 1 mCi OF Pb-212
TIME OF GROWTH OF Pb-212

| ELUTION INTERVAL (HRS) | 4 HRS | 8 HRS | 12 HRS | 24 HRS | INFINITY |
|---|---|---|---|---|---|
| 0.25 | 2.219 | 3.928 | 5.243 | 7.635 | 9.642 |
| 0.5 | 2.043 | 3.615 | 4.826 | 7.027 | 8.875 |
| 1.0 | 1.741 | 3.082 | 4.113 | 5.990 | 7.565 |
| 2.0 | 1.295 | 2.292 | 3.059 | 4.455 | 5.626 |
| 4.0 | 0.780 | 1.380 | 1.842 | 2.683 | 3.388 |

The calculated yield of Bi-212 has been found to be dependent on the elution time interval. For example, as illustrated in Table 1, eluting the column at fifteen (15) minute intervals over a twenty-four (24) hour period theoretically yields 7.635 mCi of Bi-212 for each mCi of Pb-212 initially introduced to the column.

The actual yields of Bi-212 in an above-prepared radio-impurity-free solution have been shown to vary from the calculated theoretical yields depending upon the concentration of the acid solution used to elute the Bi-212. As illustrated in Table 2, the percent of theoretical yield was shown to vary between 6.9 percent and 90.0 percent for concentrations of nitric acid between 0.1 N and 2.0 N, and between 78.0 percent and 94.0 percent for concentrations of HCl between 0.5 N and 2.0 N.

TABLE 2

COMPARISON OF ELUTIONS WITH NITRIC AND HYDROCHLORIC ACIDS

| CONC. OF ACID | PERCENT YIELD NITRIC ACID | PERCENT YIELD HYDROCHLORIC ACID |
|---|---|---|
| 0.1 N | 6.9 | |
| 0.2 N | 45.6 | — |
| 0.3 N | 65.6 | — |
| 0.5 N | 70.0 | 78 |
| 0.9 N | 79.9 | 79 |
| 2.0 N | 90.0 | 94 |

The actual yields of Bi-212 at varying elution times are shown in Table 3 below. The Bi-212 was eluted using a hydrochloric acid solution at a concentration of 0.95 N.

TABLE 3

ACTUAL YIELDS OF Bi-212 GENERATED FROM Pb-212 AT VARIOUS ELUTION TIMES

| Pb-212 (mCi) | ELUTION TIME | Bi-212 (mCi) |
|---|---|---|
| 37.2 | 1 HR. 41 MIN | 20.1 |
| 35.3 | 5 HR. 23 MIN. | 30 |
| | 2 HR. 21 MIN. | 19.9 |
| 14.5 | 38 MIN.* | 2.3 |
| 10.1 | 4 HR. 7 MIN. | 10.9 |
| | 6 HR. 40 MIN.* | 11.8 |
| 18.5 | 2 HR. 55 MIN. | 13.9 |
| 17.7 | 5 HR. 10 MIN. | 14.2 |
| | 7 HR. 43 MIN.* | 10.3 |
| 5.9 | 3 HR. 20 MIN. | 4.9 |
| 6.6 | 3 HR. 18 MIN. | 4.5 |
| 3.1 | 4 HR. 13 MIN. | 3.8 |

*Bi-212 permitted to regrow after initial elution

The solubility of Bi-212 in a radio-impurity-free solution has been observed to be dependent upon the pH value of the solution, with the solubility increasing with a decrease in pH value. The solubility was measured by passing the solution through a 0.22 $\mu$ Nalgene® filter and measuring the activity of the resulting solution and the activity of the filter. The results are presented in Table 4 below.

TABLE 4

SOLUBILITY OF Bi-212 AT VARIOUS pH VALUES

| Ph | ACTIVITY ON FILTER (mCi) | PERCENT ACTIVITY ON FILTER | ACTIVITY IN SOLUTION (mCi) | PERCENT ACTIVITY IN SOLUTION |
|---|---|---|---|---|
| 6 | 0.24 | 4 | 5.55 | 96 |
| 7 | 0.023 | 6 | 3.24 | 94 |
| 8 | 0.50 | 17 | 1.90 | 83 |
| 9 | 1.35 | 68 | 0.65 | 32 |

A substantially radio-impurity free Bi-212 solution described herein is useful in a process described below in that such a solution can effectively treat, e.g., cause the death of or otherwise retard the growth of, target cells. A particularly preferred solution includes a substantially radio-impurity free aqueous Bi-212 preparation at pH 7.4 such as that obtained by neutralizing the before-described acidic Bi-212 solution. Preferably, the acidic Bi-212 solution is neutralized using 1.0 N NaOH.

As the Bi-212 solution is neutralized, water-insoluble bismuthoxychloride (BiOCl) is formed as a dispersion in the aqueous phase. The Bi-212 in this form is uncomplexed. That is, the Bi-212 is not complexed with complexing agents such as antibodies, diethylenetriaminepentaacetic acid (DTPA) and the like.

Bismuthoxychloride is insoluble in water, but when formed as described herein, a clear composition results. It is believed that the BiOCl is present in this composition as a colloidal dispersion or other non-setting dispersion and the composition is referred to simply as a dispersion.

In addition, while being highly effective in the treatment and eradication of carcinoma, an uncomplexed Bi-212 dispersion exhibits characteristics that can make it useful in other medical treatments. It has been observed that various radionuclides such as Iridium-192, Yttrium-90 and Rhenium-188 can be useful in the treatment of arthritis and coronary heart disease because of their radioactive properties. Raloff, *Science News*, 152:40–42 (1997). An uncomplexed Bi-212 dispersion can similarly be a successful treatment preparation because of its relatively short half-life, and its even distribution characteristics.

In treating a disease condition as described above, a contemplated Bi-212 dispersion is administered or instilled into the body of the patient in need thereof, e.g., the host mammal such as a rabbit, a mouse, a rat, a dog, a primate such as a monkey, ape or human being treated, and preferably into an enclosed, cavity-like area such as into the peritoneum or the knee joint. The dispersion can also be administered into, for example, a coronary artery. The dispersion is administered in a form in which the Bi-212 is present as BiOCl.

In an anticipated use, the total dose administered to the patient in single or divided doses, such as by a continual administration can be in amounts, for example, of up to about 300 mCi over a period of about 6 hours.

The dosage regimen for treating a disease condition with a Bi-212 dispersion is selected in accordance with a variety of factors, including the type, age, weight, sex, diet and medical condition of the patient, the severity of the disease, pharmacological considerations such as the activity, efficacy, pharmacokinetic and toxicology profiles of the Bi-212 dispersion and whether the dispersion is administered as part of a drug combination. A variety of factors specific to the type of treatment can also be considered. For example, in the treatment and eradication of carcinoma, the configuration and size of the tumor is also to be considered. Thus, the dosage regimen actually employed can vary widely and therefore can deviate from the preferred dosage regimen set forth above.

As discussed above, it has been observed that Bi-212, which is an alpha particle emitter, is an effective radionuclide for use in the treatment and eradication of microscopic carcinoma such as that diseased tissue that arises from metastatic ovarian cancer. In a most effective use, the Bi-212 is maintained in solution or as part of a non-settling dispersion during its decay. It has been found that Bi-212 is maintained in solution at an acidic pH value.

Preferably, the substantially radio-impurity free Bi-212 acid solution is maintained at a pH value of about 7.4 for use. It will be recognized that the solution, as eluted from the column, is at a lower pH value than 7.4. As discussed above, the addition of a neutralizing agent, such as NaOH or another pharmaceutically acceptable base is used to neutralize the acidic Bi-212 solution to a pH value of about 7.4. The solution is administered with other ingredients such as sterile $H_2O$ to produce an isotonic solution for administration.

Previous attempts to use alpha-emitting nuclides in treating cancerous cells were unsuccessful in that such attempts used a vehicle (such as Pb-212 ferrous hydroxide) to carry the nuclide into contact with the diseased, e.g., cancerous, cells. It was observed shortly after introduction of ferrous hydroxide Pb-212, that the Pb-212 agglomerated, forming "clumps" resembling Dijon mustard. Thus, problems were encountered with the distribution of such nuclides when used with these vehicles. Similar difficulties were noted using P-32 chromic phosphate.

Unlike previous attempts to use alpha-emitting nuclides and P-32, the present Bi-212 dispersion is introduced into a confined cavity within the patient's body such as the peritoneum without an iron-based or other ion-suspending vehicle or complexing agent being required and preferably absent. Biological studies have shown that such an intraperitoneally administered Bi-212 dispersion exhibits even distribution within the peritoneal fluid. It is to be noted that the rate of decay of Bi-212 is sufficiently fast (i.e., the half-life is sufficiently short) that any "clumping", if it occurs at all, happens after the Bi-212 has decayed to its daughter products and has "delivered" its radiation to the target cells.

Biological studies were conducted to illustrate the effectiveness of Bi-212 prepared using a contemplated apparatus and process, as well as the nuclide distribution upon introduction into the peritoneal fluid, and through the duration of the decay of Bi-212. The following examples are intended to exemplify the invention and are not intended to limit the invention to the specific examples described herein.

EXAMPLE 1

In Vitro Studies

In vitro studies were carried out using three well known cell lines, the cells from which were exposed to radiation from: (1) an X-ray source; (2) P-32 chromic phosphate; and (3) Bi-212 chloride. The three cell lines that were used are V-79, which is a Chinese hamster lung fibroblast, Ehrlich-Lettre Ascites carcinoma (ATCC CCL 77), which is an ascites producing -tumor, and NIH:OVCAR-3 (ATCC HTB 161), which is a human ovarian adenocarcinoma. These well known cell lines are predictive of what happens in vivo. The cells were grown as monolayers and into spheroid formations and subsequently irradiated, as described herein.

The V-79 cells were maintained under exponential growth conditions in minimal essential medium (MEM) supplemented with 10 percent fetal bovine serum. The Ehrlich-Lettre Ascites carcinoma cells were maintained in 90 percent NCTC 109 supplemented with 10 percent fetal bovine serum. The NIH:OVCAR-3 cells were maintained in RPMI 1640 and 10 percent fetal bovine serum.

To initiate the formation of the spheroids, cells at a concentration of about 500,000 cells per flask were seeded onto petri dishes base-cooked with 1 percent agar MEM without serum. After spheroids having a size of about 20 micrometers ($\mu$m) formed, the spheroids were transferred to spinner bottles and maintained for two to three weeks at a temperature of 37° C. in a $CO_2$ incubator until they grew to 10 to 1000 $\mu$m. Prior to irradiation, the spheroids were sized and separated using a spheroid separation column.

Cells from each of the cell lines were irradiated by subjecting the cells to X-ray radiation, P-32, and Bi-212. The X-ray source that was used is a General Electric 250 kvp Maxitron, 26 milliAngstroms (mA) (HVL 1.5 mm Cu) operated at a dose rate of 1.11 Greys per minute (Gy/min). The cells, in both monolayer and spheroid form were exposed at room temperature and then immediately plated for survival.

Cells in both monolayer and spheroid were exposed to P-32 chromic phosphate. The radiation dose to each sample was calculated as:

$$D_{\beta,t}=73.8 C\overline{E}_\beta T_{1/2}(1-e^{-(0.693t/T_{1/2})})cGy,$$

where $D_{\beta,t}$=dos at time t,

C=initial concentration of P-32 in microCuries per gram ($\mu$Ci/gm) at the beginning of time t, $\overline{E}_\beta$=0.695 MeV, and $T_{2/3}$=14.3 days (half-life of P-32).

After exposure, the cells were washed in phosphate-buffered saline (PBS) and immediately plated for survival.

The cell lines were also irradiated using Bi-212. Bismuth-212 was eluted from a generator as described in the aforementioned patent to Atcher et al., which was a cation-exchange column supporting Ra-224, with 1 ml of 0.15 N HI, and the generator was purged with 2 ml of distilled deionized water. The acid was neutralized to pH 5 with 150 ml of 4 N sodium acetate and sterilized by passage through a 0.22-$\mu$m Millex-GV filter. In some experiments, 50 ml of 100 mM diethylenetriaminepentaacetic acid (DTPA) was added and the reaction mixture shaken before filter sterilization. The filter was purged with 1 ml of distilled deionized water, and the radioactivity was assayed using a calibrated 3×3-in. NaI detector. The detector output was fed into a 4096 channel analyzer. The 583-keV gamma from thallium-208 (Tl-208) was used to determine the Bi-212 activity. The Tl-208 is a source that is traceable to the National Bureau of Standards.

Cells were exposed over a period of four hours. The dose (D) per microCurie was calculated and corrected for decay as follows:

$$D = \frac{(1.33 \times 10^8 \text{ dis/hr}/\mu\text{Ci}) \times 7.8 \text{MeV} \times 1.6 \times 10^{-6} \text{ erg/MeV}}{V \times 100 \text{erg/ml-cGy}}$$

where

V=volume in milliliters, and

D in calculated in cGy/$\mu$Ci-hr

The dose calculations were made presuming that the Bi-212 uniformly distributed throughout the sample during the period of exposure.

Following plating, survival measurements were taken for each of the irradiated cell samples. The cells were first trypsinized. Between 100 and 20,000 cells were placed in 10 milliliters (mL) of compete medium in petri dishes. The plates were incubated at 37° C. for seven to ten days. The plates were then stained with crystal violet and colonies greater than 50 cells were scored. The surviving fraction was then determined.

Figure 5:
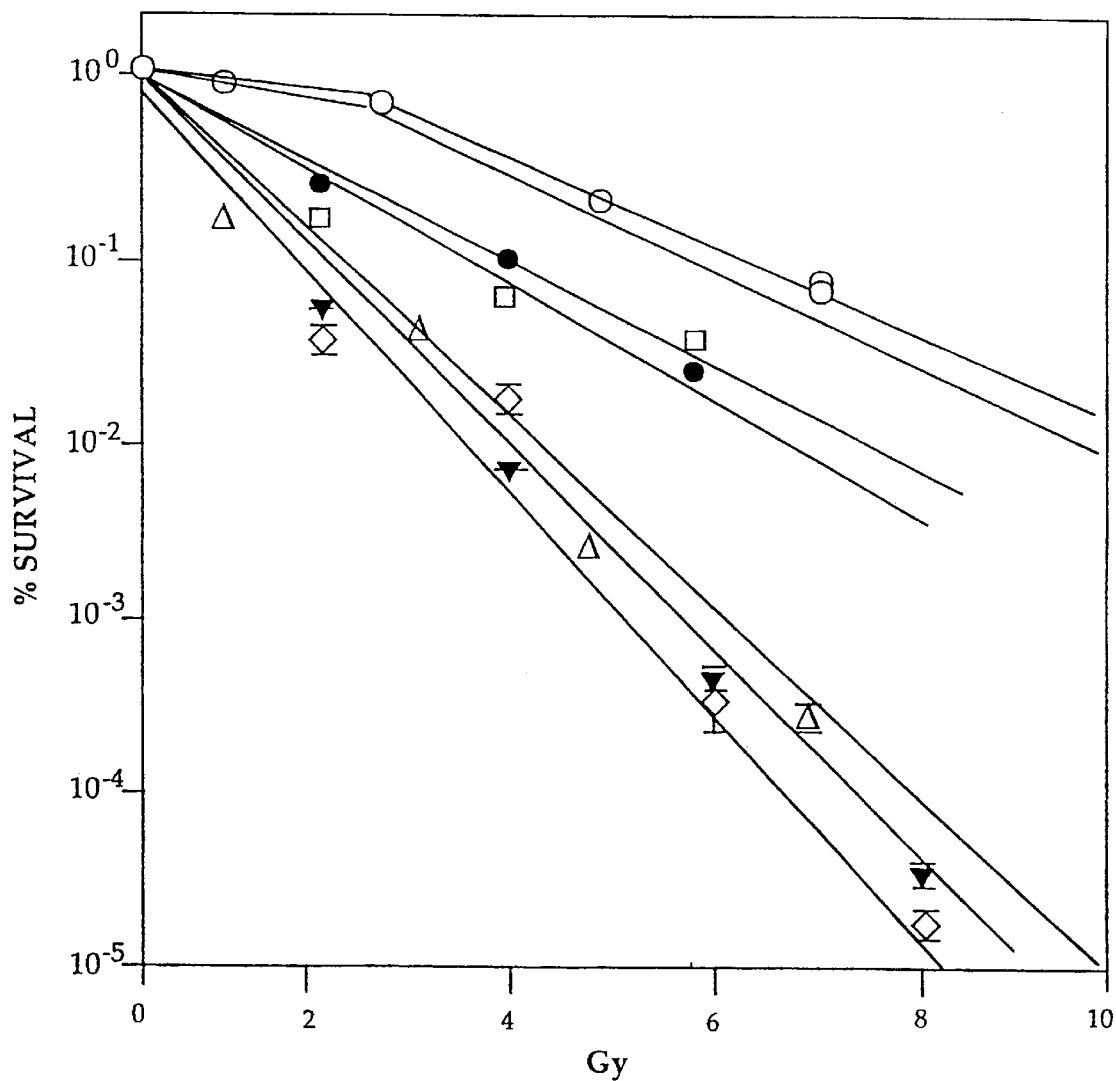
FIG. 5 is a graphic illustion of the percent of cells surviving as a function of the radiation dose received in Greys (Gy) of monolayer cells of V-79 subjected to X-ray radiation (open hexagons), V-79 cells subjected to P-32 chromic phosphate (open squares), V-79 cells subjected to Bi-212 (open triangles), Ehrlich-Lettre Ascites carcinoma cells subjected to Bi-212 (open diamonds), OVCAR-3 cells subjected to X-ray radiation (open circles), OVCAR-3 cells subjected to P-32 chromic phosphate (filled circles) and OVCAR-3 cells subjected to Bi-212 (filled, inverted triangles)
Figure 6:
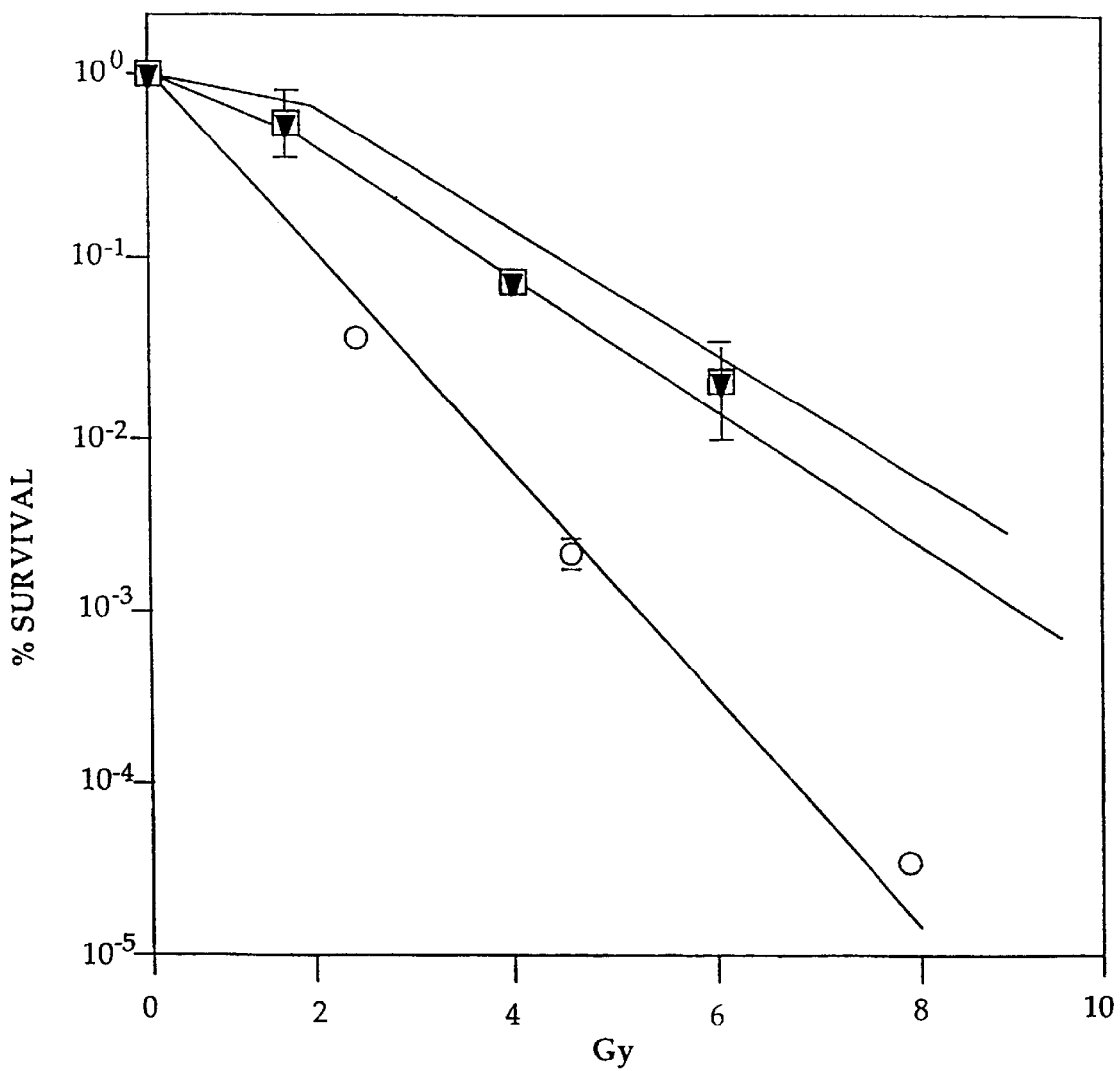
FIG. 6 is a graphic illustration of the percent of cells surviving as a function of the radiation dose received in Gy of 800 $\mu$m spheroids of OVCAR-3 cells that were subjected to X-ray radiation (filled, inverted triangles), P-32 chromic phosphate (open squares) and Bi-212 (open circles)

Intrinsic radiosensitivity ($D_o$) was calculated from the survival curves. The mean lethal dose increment that was needed to reduce the surviving population after treatment to 37 percent of the previous level along the straight line portion of the survival curve was used to calculate $D_o$. FIGS. 5 and 6 graphically illustrate the survival curves for irradiated cell lines of V-79, Ehrlich-Lettre Ascites carcinoma and OVCAR-3 in monolayer and spheroid cell formations. Relative biological effectiveness (RBE) was determined as the ratio of the absorbed dose of X-ray to that of alpha radiation to produce the same degree of biological effect. Table 5, below, shows a comparison of the radiosensitivities and relative biological effectiveness values that were calculated based upon the cell samples studied.

TABLE 5

COMPARISON OF RADIOSENSITIVITY ($D_0$) AND RELATIVE BIOLOGICAL EFFECTIVENESS (RBE)

| | $D_0$ X-RAY (in Gy) | $D_0$ P-32 (in Gy) | RBE P-32 | $D_0$ Bi-212 (in Gy) | RBE Bi-212 |
|---|---|---|---|---|---|
| MONOLAYER | | | | | |
| OVCAR-3 | 1.50 | 1.40 | 1.43 | 0.75 | 3.19 |
| V-79 | 1.55 | 1.25 | 1.63 | 0.77 | 3.02 |
| EHRLICH SPHEROIDS | — | — | — | 0.65 | — |
| OVCAR-3 | 1.1 | 1.1 | 1.07 | 0.55 | 2.81 |

As can be seen from an examination of the data in Table 5, cells of HIV:OVCAR-3 in both monolayer and spheroid form, and cells of V-79 in monolayer form that were irradiated with Bi-212 showed considerably higher relative biological effects than those cells that were exposed to X-rays and radiation from P-32. That is, the relative biological effectiveness using Bi-212 was shown to be 3.19, 2.81 and 3.02. respectively, compared to X-ray irradiation.

Likewise, the dose required to achieve equal cell survival rates was significantly lower for those cells exposed to Bi-212 compared to those cells exposed to X-rays and radiation from P-32. For example, the dose rate to achieve a 37 percent survival rate for the NIH:OVCAR-3 cells in spheroid form was 0.55 Gy for Bi-212 compared to 1.1 Gy for X-ray and P-32 irradiation; that is, one-half of the dose required by X-ray and P-32 irradiation was needed to achieve the same survival rate for cells exposed to Bi-212.

Various spheroid formation cell samples were examined using both electron microscopy and autoradiography. Samples were prepared for electron microscopy by placing the cells in 2 percent glutaraldehyde and 2 percent formaldehyde electron microscopy grade in phosphate buffered saline (PBS) at a pH of 7.4 for ten minutes at room temperature. The spheroids were then transferred to glass vials and placed in an ice bath for ten minutes. Subsequently, the spheroid samples were washed with 0.2 M sucrose in 0.1 M $PO_4$, fixed in 1 percent $OsO_4$ in 0.1 M phosphate and gently mixed for two hours as 4° C. After 24 hours, the cell samples were dehydrated with alcohol, fixed in upon and scanned by electron microscopy.

Spheroid cell samples that were exposed to Bi-212 were prepared for autoradiography after a two hour exposure to Bi-212. The samples were washed with PBS, frozen, dehydrated, fixed in acetone and sectioned. Thin-layer sections were dipped in NTB-3 emulsion (commercially available from Kodak Corp. of Rochester, N.Y.), diluted 1:1 with distilled water and heated to 42–44° C. for 10–20 minutes. The cell samples were then developed in D1 developer (also available from Kodak Corp.), stained with hematoxylin and eosin and examined using autoradiography.

EXAMPLE 2

In Vivo Studies

In vivo studies were conducted to determine the distribution of Bi-212 produced using the above-noted process and to compare the Bi-212 distribution to the distribution of Pb-212 ferrous hydroxide in colloidal form. The in vivo studies were conducted using white, female New Zealand rabbits weighing about 4.5 kilograms (about 2 pounds) each. Studies were also conducted using rabbits to determine the toxicity levels, e.g., the maximum tolerated dose. Efficacy studies were conducted using 25 gram (gm) female Swiss-Webster mice inoculated with Ehrlich-Lettre Ascites carcinoma cells. The results of these studies are presented below.

Distribution Studies

The rabbits were first anesthetized by intravenous titration. A polyethylene catheter was then inserted into the lower right quadrant of the rabbits' abdominal cavities and a trace amount of technetium-99m pertechnetate was instilled to confirm that the catheter was correctly placed.

Groups of rabbits were instilled with a varying amounts (correlating to varying activities) of Bi-212 that were prepared in accordance with the before-described process, neutralized to pH values of between 5.0 and 7.4, and had added thereto a quantity of normal saline to make a 200 cc sample. To compare the distribution of Bi-212, Pb-212 ferrous hydroxide was prepared in accordance with known methods. Rotmensch et al., *Gynecol. Oncol.*, 35:297–300 (1989). Groups of rabbits were also instilled with the Pb-212 ferrous hydroxide preparation.

After instillation, the rabbits were rotated and imaged with a gamma camera set at 2.6 MeV. Where localization of the nuclide was identified in the rabbits, the rabbits were sacrificed and the localized area was excised and photographed.

Of the groups of rabbits instilled with the Bi-212 solution, a rabbit was imaged and necropsied at each of one-half hour, one hour and three hours after instillation. The percent injected activity (%IA) in each organ was measured to determine the distribution of the Bi-212(Table 6). To determine whether chelating to DTPA improved the retention of Bi-212 in the peritoneal fluid, a group of rabbits was instilled with Bi-212 DTPA, and was imaged and necropsied at three hours following instillation. The percent activity remaining in the peritoneal fluid was measured. The results of this comparison are shown in Table 7.

It was observed that the distribution of Bi-212 was relatively even when compared to the non-uniform distribution of Pb-212 ferrous hydroxide. At necropsy of the rabbits that were instilled with the Pb-212 preparation, clumps of iron particles were found on peritoneal and bowel surfaces.

Imaging of the rabbits that were instilled with Bi-212 shows no clumping; i.e., no localized activity in the peritoneal cavity up to 3 hours after instillation. Rabbits that were necropsied at one-half hour, one hour and 3 hours after instillation showed that 85.1 percent to 88 percent of the activity remained in the peritoneal fluid rather than accumulating in various organs. Table 6, below, shows the distribution of Bi-212 in percent injected activity at one-half hour, one hour and 3 hours after instillation. Surprisingly, as shown in Table 7, an examination of the rabbits that were instilled with the Bi-212 DTPA showed that only 51 percent of the activity remained in the peritoneal cavity at 3 hours after instillation.

TABLE 6

BIODISTRUBTION OF Bi-212 AT ½, 1 AND 3 HOURS AFTER INTRAPERITONEAL INSTILLATION

| ORGAN | ½ HOUR (% IA) | | | 1 HOUR (% IA) | | | HOUR (% IA) | | |
|---|---|---|---|---|---|---|---|---|---|
| | #1 | #2 | #3 | #1 | #2 | #3 | #1 | #2 | #3 |
| PER. FLUID | 85.0 | 70.3 | 90.1 | 85.7 | 85.1 | 88 | 75.8 | 80.2 | 83.8 |
| LIVER | 0.68 | 0.63 | 0.18 | 1.45 | 0.41 | 0.23 | 2.26 | 2.25 | 1.17 |
| KIDNEY | 0.74 | 0.98 | 0.19 | 1.59 | 0.53 | 0.34 | 2.15 | 1.21 | 2.10 |
| REPR. | 0.63 | 0.09 | 0.09 | 0.40 | 0.04 | 0.08 | 0.53 | 0.61 | 0.59 |
| STOM. | — | 0.26 | 0.34 | — | — | 0.09 | 0.90 | 0.76 | 0.59 |
| LOWER INTES. & COLON | 3.36 | 1.90 | 0.53 | — | — | 0.87 | 7.14 | 5.87 | 9.14 |
| UP. SM. INTES. | 4.35 | 2.16 | 0.87 | 5.24 | 2.28 | 0.96 | 8.04 | 6.63 | 9.73 |
| CIRC. BLOOD | 1.23 | — | 0.22 | 2.22 | 1.17 | 0.44 | 3.4 | 1.86 | 2.96 |
| RED MARROW | 0.05 | 0.10 | 0.03 | — | — | — | 0.20 | 0.20 | 0.09 |
| CARC. | 15.3 | 5.90 | 1.33 | 40.2 | 1.70 | 2.17 | 8.70 | 4.01 | 4.89 |
| VOL. PER. FL. RECOVER (ml)* | 183 | 168 | 184 | 142 | 162 | 167 | 188 | 200 | 192 |

*Initial volume = 200 ml
(Per - peritoneal; Repr. - reproductive; Stom. - stomach; Intes. - intestine; Up Sm. - upper small; Circ. - circulating; Carc. - carcass)
IA = injected activity

TABLE 7

COMPARISON OF RETENTION OF CHELATED AND NON-CHELATED Bi-212 IN PERITONEAL FLUID

| | % ACTIVITY IN PERITONEAL FLUID | % ACTIVITY IN BLOOD VOLUME | % ACTIVITY IN URINE |
|---|---|---|---|
| Bi-212 | 80 | 4.5 | 6.0 |
| Bi-212-DTPA | 51 | 9.4 | 40 |

Toxicity Studies

The peritoneal cavities of rabbits were instilled with graded doses of Bi-212. The rabbits were followed until death or for up to three months after their blood counts normalized. The rabbits were necropsied at death or termination of the study and their organs were microscopically examined to determine the effect of the Bi-212 on healthy organs.

It was observed that the maximum dose of Bi-212 tolerated by the rabbits was 60 mCi. At 60 mCi, microscopic examination of organs three months after instillation showed only mild blunting of intestinal villi. Doses greater the 60 mCi caused death within three days. At 80 mCi, the rabbits survived about three days and exhibited marked individual cell necrosis of gland epithelium of the small and large intestines. At a dose of 100 mCi, the rabbits survived about three days and exhibited diffuse epithelial necrosis.

Efficacy Studies

Efficacy studies were conducted using groups of five 25 gm female Swiss-Webster mice that were intraperitoneally inoculated with $10^6$ Ehrlich-Lettre Ascites carcinoma cells. The mice were subsequently instilled with 100 $\mu$Ci of Bi-212 in up to 1 cc normal saline 48 hours after inoculation with the Ehrlich-Lettre Ascites carcinoma cells. The mice were sacrificed at one-half hour, one hour and 3 hours after instillation with the Bi-212 solution. Control groups were inoculated with the Ehrlich-Lettre Ascites carcinoma cells only.

It was observed that the maximum tolerated dose in the mice was 0.65 mCi. As shown in Table 8, below, necropsying the mice at one-half hour, one hour and 3 hours after instillation of the Bi-212 solution showed that 61.4 percent of the activity remained in the mice at 3 hours after instillation. Examination of mice in the control group revealed that solid nests of tumor cells formed and infiltrated the tissue within 48 hours after inoculation.

Figure 7:
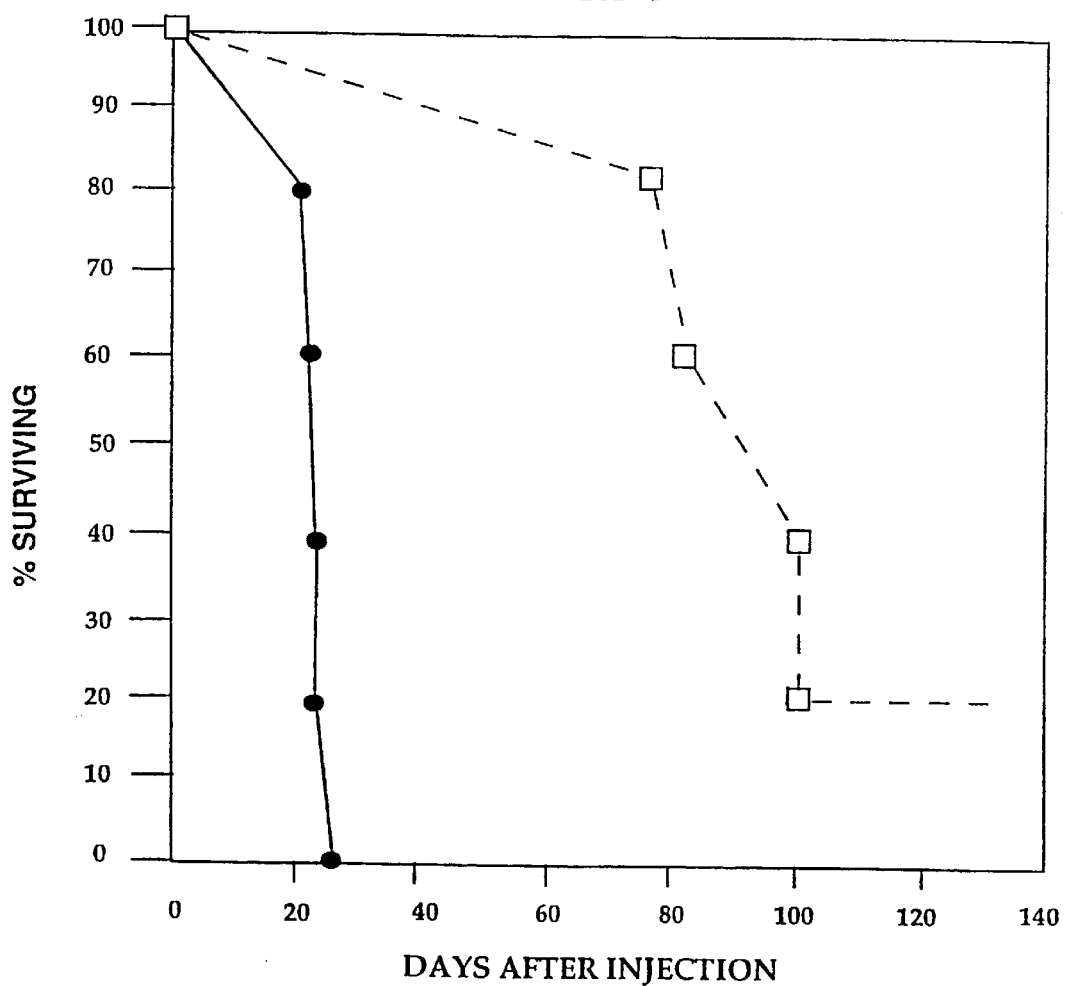
FIG. 7 is a graphic illustration of the percent of mice that survived, as a function of days following injection, that were injected with $10^6$ Ehrlich-Lettre Ascites carcinoma cells (filled circles) and mice that were injected with $10^6$ carcinoma cells and subsequently treated with 100 $\mu$Ci of Bi-212.

The mice in the control group died within 21 days. Mice that were treated with Bi-212 had a median survival time of 82 days after treatment. In 40 percent of the mice, there is a cure with no evidence of disease 3 months later. The results are illustrated graphically in FIG. 7.

TABLE 8

RETENTION OF Bi-212 AFTER INTRAPERITONEAL INJECTION IN MICE

| SACRIFICE TIME (MIN) | CARCASS % IA | URINE % IA | STOOL % IA |
|---|---|---|---|
| 1 | 88.3 | 0.025 | — |
| 10 | 87.3 | 2.2 | — |
| 16 | 66.8 | 2.9 | 0.20 |
| 30 | 79.1 | 6.9 | 0.53 |
| 61 | 68.5 | 15.9 | 1.3 |
| 120 | 62.9 | 19.5 | 6.7 |
| 180 | 61.4 | 24.8 | 8.3 |

Based upon the in vivo studies, a contemplated dose of 100 mCi to a human produces an alpha and gamma dose to any organ of less than 150 cGy. The calculated alpha dose to the gastrointestinal tract, liver and kidneys is 87.7, 24.6 and 92.5 cGy, respectively, and the calculated gamma dose is 7.39, 4.14 and 5.00 cGy, respectively. Table 9, below, provides the estimated total dose in humans based upon an initial dose of 100 mCi of Bi-212.

TABLE 9

ESTIMATED TOTAL DOSE IN HUMANS/100 mCi OF Bi-212

| ORGAN | GAMMA DOSE/ 100 mCi | ALPHA DOSE/ 100 mCi | TOTAL DOSE |
| --- | --- | --- | --- |
| RED MARROW | 2.30 | 2.45 | 4.75 |
| BRAIN | 0.038 | 2.45 | 2.49 |
| BREASTS | 0.643 | 2.45 | 3.09 |
| GI TRACT | 7.39 | 87.7 | 95.1 |
| KIDNEYS | 5.00 | 92.5 | 97.5 |
| LIVER | 4.14 | 24.6 | 28.7 |
| LUNGS | 1.33 | 2.45 | 3.78 |
| OVARIES | 5.42 | 102.4 | 107.8 |
| PANCREAS | 17.2 | 2.45 | 19.7 |
| THYROID | 0.154 | 2.45 | 2.60 |
| UTERUS | 21.2 | 102.4 | 123.6 |
| REMAINDER | 1.78 | 2.45 | 4.23 |
| TOTAL BODY | 1.83 | 2.45 | 4.28 |

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A process for producing substantially radio-impurity-free Bi-212 comprising the steps of:
   (a) contacting an acidic Pb-212 feed solution with an extraction medium having a plurality of binding sites thereon adapted to bind said Pb-212 thereto, to form a Pb-212-laden extraction medium and less strongly bound contaminants;
   (b) rinsing said Pb-212-laden extraction medium with a second acid solution to remove the less strongly bond contaminants therefrom and to form a substantially impurity-free Pb-212-laden extraction medium;
   (c) maintaining said substantially radio-impurity-free Pb-212-laden extraction medium for a predetermined period of time so as to form Bi-212 from said Pb-212 by radioactive decay;
   (d) introducing a third acid solution to said substantially impurity-free Pb-212-laden extraction medium to release said Bi-212 therefrom and form a Bi-212 acid solution; and
   (e) eluting said Bi-212 acid solution from said substantially impurity free Pb-212-laden extraction medium to form a substantially radio-impurity free Bi-212 acid solution.

2. The process for producing substantially impurity-free Bi-212 in accordance with claim 1 including contacting said substantially radio-impurity-free Bi-212 acid solution of step (e) with a second extraction medium having a plurality of binding sites thereon adapted to bind Pb-212 thereto.

3. The process for producing substantially impurity-free Bi-212 in accordance with claim 1 including eluting said Bi-212 from said substantially impurity free Pb-212-laden extraction medium at intervals of about two hours.

4. The process for producing substantially impurity-free Bi-212 in accordance with claim 1 including neutralizing said substantially radio-impurity free Bi-212 acid solution.

5. The process for producing substantially impurity-free Bi-212 in accordance with claim 1 wherein said Pb-212 acidic feed solution is a first acid solution containing Pb-212 or a Pb-212 generating material.

6. The process for producing substantially impurity-free Bi-212 in accordance with claim 1 wherein said first acid solution has a concentration of about 0.5 N to about 4.0 N.

7. The process for producing substantially impurity-free Bi-212 in accordance with claim 1 wherein said second acid solution has a concentration of about 0.5 N to about 4.0 N.

8. The process for producing substantially impurity-free Bi-212 in accordance with claim 1 wherein said third acid solution has a concentration of about 0.5 N to about 1.5 N.

9. The process for producing substantially impurity-free Bi-212 in accordance with claim 1 wherein said extraction medium is a solid phase-supported extractant.

10. A process for producing substantially radio-impurity-free Bi-212 comprising the steps of:
    (a) contacting an acidic Pb-212 feed solution with a solid phase-supported extractant having a plurality of binding sites thereon adapted to bind said Pb-212 thereto, to form a Pb-212-laden extractant and less strongly bound contaminants;
    (b) rinsing said Pb-212-laden extractant medium with a second acid solution to remove the less strongly bound contaminants therefrom and to form a substantially impurity-free Pb-212-laden extractant;
    (c) maintaining said substantially radio-impurity-free Pb-212-laden extractant for a predetermined period of time so as to form Bi-212 from said Pb-212 by radioactive decay;
    (d) introducing a third acid solution to said substantially impurity-free Pb-212-laden extractant medium to release said Bi-212 therefrom and form a Bi-212 acid solution; and
    (e) eluting said Bi-212 acid solution from said substantially impurity free Pb-212-laden extractant to form a substantially radio-impurity free Bi-212 acid solution.

11. An apparatus for producing substantially radio-impurity-free Bi-212 from a starting material having Pb-212 or a Pb-212 generating material comprising:
    an extraction medium having a plurality of binding sites thereon, said binding sites having an affinity for binding Pb-212 thereto and having a lower affinity for binding Bi-212 thereto;
    a first acid supply in flow communication with said extraction medium, said acid supply adapted to supply a first acid to carry the Pb-212 to said extraction medium;
    a first vessel adapted to retain said extraction medium and further adapted to maintain contact between said extraction medium and said acid;
    a second acid supply in flow communication with said vessel, said acid supply adapted to supply a second acid to said vessel;
    a mixing chamber in flow communication with said vessel adapted to receive a liquid solution therefrom, said mixing chamber having a plurality of input means connected thereto; and
    a discharge line in flow communication with said mixing chamber.

12. The apparatus in accordance with claim 11 further including a second vessel adapted to retain a quantity of extraction medium therein and further adapted to maintain contact between said extraction medium and said acid, said second vessel being in flow communication with said first vessel and in flow communication with said mixing chamber.

13. The apparatus according to claim 11 wherein said apparatus includes a pair of first vessels wherein only one of the pair of first vessels is operable at a time.

14. The apparatus according to claim 11 including a plurality remotely actuated valves therein.

15. The apparatus according to claim 11 wherein said apparatus includes a solid phase-supported extractant.

16. A process for treating target cells that comprises contacting the target cells with a biologically effective amount of a pharmaceutically acceptable composition comprising substantially impurity-free Bi-212 in solution.

17. The process in accordance with claim 16 wherein the Bi-212 is uncompleted.

18. The process in accordance with claim 16 wherein the target cells are a microscopic carcinoma.

19. The process in accordance with claim 16 wherein the target cells are within a host mammal.

20. The process in accordance with claim 19 wherein the Bi-212 is administered intraperitoneally to contact the target cells.

21. A pharmaceutical composition for the treatment of carcinoma comprising a biologically effective amount of substantially radio-impurity free Bi-212.

22. The pharmaceutical composition in accordance with claim 21 wherein the Bi-212 is uncomplexed.

23. The pharmaceutical composition in accordance with claim 21 wherein the carcinoma is a microscopic carcinoma.

24. The pharmaceutical composition in accordance with claim 21 that is administered intraperitoneally.

* * * * *

UNITED STATES PATENT AND TRADEMARK OFFICE
CERTIFICATE OF CORRECTION

PATENT NO. : 6,126,909
DATED : October 3, 2000
INVENTOR(S) : Rotmensch et al.

It is certified that error appears in the above-identified patent and that said Letters Patent are hereby corrected as shown below:

At column 5, line 67, please correct "1700" to read --170°-- ;
At column 10, line 31, please correct "[Pb]20" to read --[Pb]0-- ;
At column 10, line 51, please correct "S.243" to read --5.243--;
At column 14, line 9, please correct "=dos" to read --=dose--;
At column 14, line 16, please correct "2/3" to read --1/2--;
At column 18, line 54, please correct "66.8" to read --86.8-- ;
At column 21, line 10, please correct "uncompleted" to read --uncomplexed--.

Signed and Sealed this

First Day of May, 2001

*Attest:*

NICHOLAS P. GODICI

*Attesting Officer*     Acting Director of the United States Patent and Trademark Office